United States Patent [19]

Siri

[11] Plant 5,217

[45] Apr. 10, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,115

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation characterized by blossoms which are of a champagne color turning white, with occasional purple flecks.

2 Drawing Figures

BACKGROUND OF THE NEW PLANT

This invention comprises a new and distinct miniature carnation variety that has its own set of characteristics that set it apart from all other varieties of miniature carnations. The newly discovered variety, called "Champagne," originated as a sport of Aquarius, an unpatented variety.

The botanical classification of the new variety is *Dianthus caryophyllus longicaulis*. The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
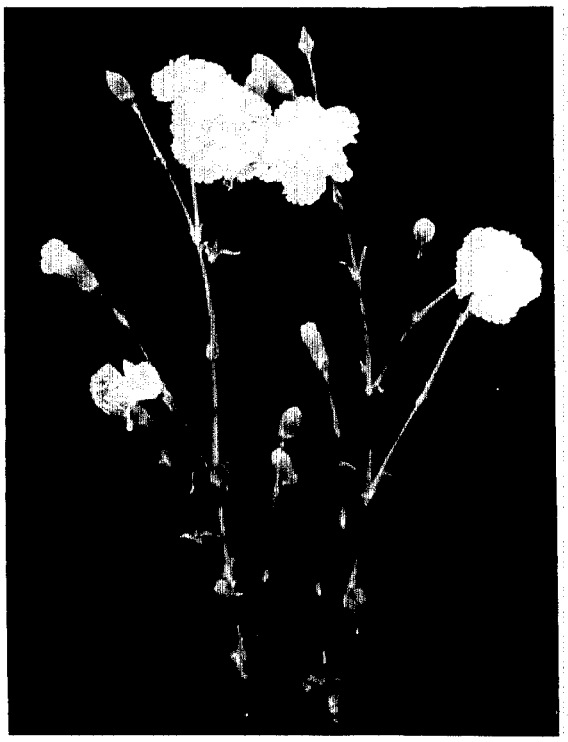
FIG. 1. PRIOR ART
FIG. 1 shows on the left a spray of the prior Aquarius and on the right a spray of new variety Champagne.
Figure 2:
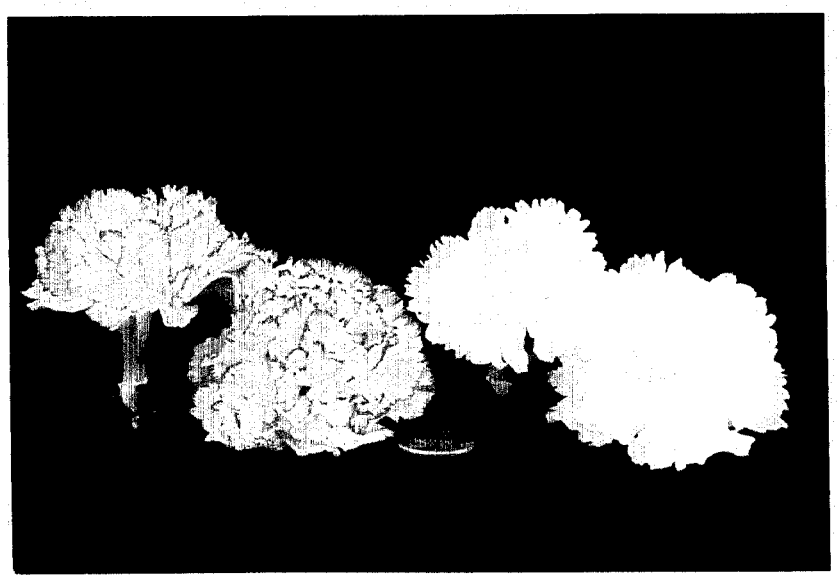
FIG. 2 shows on the left the bloom of the prior Aquarius and on the right the bloom of the new variety Champagne.

The following detailed description of the new variety is based on my detailed observations of the new cultivar which were made at Siri Brothers Nursery Inc., at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore Md. and "R.H.S." for Royal Horticultural Colour Chart, The Royal Horticultural Society, London, England.

GROWTH HABITS

Height: Average.

Foliage: More dense than average.

Speed of growth: Slower than average.

Root System: Good, better than average.

FOLIAGE

Leaf size:

*Length.*—Average length at mid-stem $4\frac{1}{4}$ inches.

*Width.*—Average width at mid-stem $\frac{3}{8}$ of an inch.

*Features.*—N/A.

Leaf shape: Average curl with a long acuminating tip.

Leaf texture: Smooth and Leathery.

Leaf color:

*Upperside.*—R.H.S. Green Group 139A with a whitish color over the green.

*Underside.*—R.H.S. Green Group 139A with a whitish color over the green.

Leaf ribs: One rib down the center from the base to the tip of the leaf.

Leaf habit: Average curl.

Leaf density: More dense than average.

STEM

Stem strength: Stronger than average.

Stem color: R.H.S. Green Group 139A with a whitish color over the green.

Nodes:

*Alternatives.*—Average.

*Space between nodes.*—Approximately 3 inches at mid-stem.

Stem branching: Very good, not clubby.

BUDS

Bud shape: Oval.

Bud color: Top half of bud LCC H-21 L-14, bottom half blends into LCC H-23 L-9.

Average number of flowering buds per stem: 5 .

Uniformity of bud opening: Very uniform.

Bud splitting: Very seldom.

Number of sepals per calyx: 90% of calyxs have 5; 10% of calyxs have 6.

FLOWER

Description of the color of the bloom: The bloom is champagne color, R.H.S. Yellow Green Group 150D especially in the center. As they age, they turn substantially white. It also has purple specks on the bloom. There are two shades of purple specks. One is a light purple LCC H-46 L-8 and the other is a dark purple LCC H-43 L-13. Most of the specks, about 95%, are the light purple and are located on the fringe of the bloom. The dark purple specks are vey few and are found more at random on the petal. The purple in the bloom seems to appear more in the winter months than in the summer. Blooms can exhibit no purple whatsoever.

General tonality of the color: Soft yet bright.
Diameter of average bloom: 2 inches.
Bloom shape: Generally round with a high center and flat outer petals.
Keeping quality: Average.
Fragrance: Very noticeable, more than average.

PETALAGE

Petal texture: Soft and velvety.
Petal edge: Very serrated.
Color stability: Very stable, only very slight reversion to Aquarius.
Petal size:
*Average length.*—1¾ inches.
*Average width at widest point.*—1 inch.
Calyx color: The top half of the calyx is LCC H-21 L-14 and the bottom half blends into LCC H-22 L-9. The tips of the leaves on the bottom of the calyx are LCC H-17 L-15.

REPRODUCTIVE ORGANS

Stamen: With anthers.
Average length of stamen: 1-1/16 inches.
Color of anthers: LCC H-25 L-2.
Color of filament: LCC H-25 L-1.
Pistils:
*Shape.*—Approximately 100% have two styles.
*Number.*—One.
*Length from tip to ovary.*—1⅜ inches.
Stigma:
*Shape.*—Round.
*Color.*—White, it is located at the very tip of the style.
Style:
*Color.*—LCC H-25 L-1.
Ovary:
*Shape.*—Ovid.
*Color.*—The top half is LCC H-23 L-7, the bottom half is LCC H-23 L-1.
*Length.*—⅜ of an inch.
*Width.*—¼ of an inch.

DISTINGUISHING CHARACTERISTICS BETWEEN THE NEW VARIETY AND PARENT

The only distinguishing characteristic between the new variety and the parent is the color.

SIMILAR CHARACTERISTICS OF THE NEW VARIETY AND PARENT

All of the characteristics of both varieties are similar except for the distinguishing characteristics referred to above.

I claim:

1. A new and distinct variety of miniature carnation plant, substantially as herein shown and described.

* * * * *

PRIOR ART